United States Patent [19]

Jessel, Jr. et al.

[11] Plant 4,005

[45] Jan. 4, 1977

[54] CHRYSANTHEMUM PLANT

[75] Inventors: Walter H. Jessel, Jr., Doylestown; William E. Duffett, Akron, both of Ohio

[73] Assignee: Yoder Brothers, Inc., Barberton, Ohio

[21] Appl. No.: 658,852

[22] Filed: Feb. 18, 1976

[51] Int. Cl.[2] ..... A01H 5/00

[52] U.S. Cl. ..... Plt./75

[58] Field of Search ..... Plt./74–75, Plt./79

*Primary Examiner*—Robert E. Bagwill
*Attorney, Agent, or Firm*—Donald D. Jeffery

CLAIM

A new and distinct cultivar of chrysanthemum known by the cultivar name Revere and characterized particularly as to uniqueness by the combined characteristics of flat inflorescence form, reflexing slightly at maturity; pompon inflorescence type; two-toned red bronze and yellow bronze inflorescence color; diameter across face of inflorescence up to 2.75 inches; permanence of inflorescence ranging from 14 to 21 days; medium plant height; semi-upright branching pattern; average natural season flowering date of September 30 and average flowering response period of 7 weeks in photoperiodic controlled flowering programs.

3 Drawing Figures

The present invention comprises a new and distinct cultivar of Chrysanthemum morifolium, Ramat., hereinafter referred by the cultivar name Revere (No. 74045001).

Revere is a product of a planned breeding program which had the objective of creating cultivars with small pompon inflorescence type, short height, spreading branching pattern, durable inflorescence, short (6 to 7 week) flowering response period, and adaptability of both natural season outdoor flowering and controlled greenhouse flowering programs.

Revere was originated from a cross made in a controlled breeding program in Barberton, Ohio in the year 1973. The male, or pollen parent, was No. 73337003 (unnamed seedling), a red bronze pompon originated by the present inventors from a cross between No. 72074M01 (unnamed seedling) and No. 72018003 (unnamed seedling). The female, or seed parent of Revere, was No. 73247002 (unnamed seedling), an orange bronze pompon originated by the present inventors from a cross between No. 72037009 (unnamed seedling) and No. 72018003 (unnamed seedling).

Revere was discovered and selected as a flowering plant within the progeny of the stated cross by Walter H. Jessel, Jr. on May 4, 1974 in an outdoor field in Ft. Myers, Florida.

The first act of asexual reproduction of Revere was accomplished when vegetative cuttings were taken from the initial selection in July, 1974 in a controlled environment in Barberton, Ohio by a technician working under formulations established and supervised by William E. Duffett and Walter H. Jessel, Jr. Horticultural examination of selected units initiated Oct. 10, 1974 has demonstrated that the combination of characteristics as herein disclosed for Revere are firmly fixed and are retained through successive generations of asexual reproduction.

Revere has not been observed under all possible environmental conditions. The phenotype may vary significantly with variations in environment such as temperature, light intensity, and daylength. The following observations, measurements, and comparisons describe plants grown in a field in Barberton, Ohio under conditions which are generally described in *Local Climatalogical Data, Annual Summary with Comparative Data*, Akron, Ohio. U.S. Department of Commerce, National Oceanic and Atmospheric Administration, Environmental Data Service, Washington, D.C. 1974, 1975 and *Tables of Sunrise, Sunset, and Twilight*. Supplement to the American Emphemeris, 1946, U.S. Naval Observatory, Washington, D.C., pg. 103.

The following traits have been repeatedly observed and are determined to be basic characteristics of Revere which in combination distinguish this chrysanthemum as a new and distinct cultivar:

1. Flat inflorescence form, reflexing slightly at maturity.
2. Pompon inflorescence type.
3. Two-toned red-bronze to yellow-bronze inflorescence color.
4. Diameter across face of inflorescence up to 2.75 inches.
5. . Permanence of inflorescence ranging from 14 to 21 days.
6. Medium plant height.
7. Semi-upright branching pattern.
8. Average natural season flowering date of September 30.
9. Average flowering response period of 7 weeks in photoperiodic controlled flowering programs.

The accompanying photographic drawings show typical inflorescence and foliage characteristics of Revere with colors being as nearly true as possible with illustration of this type. Sheet 1 is a color photograph of Revere. Sheet 2 is a black and white photograph showing three views of the inflorescence of Revere. Sheet 3 is a black and white photograph showing the foliage of Revere at three stages of growth.

Of the many commercially available cultivars known to the present inventors, the most similar existing cultivars in comparison to Revere are Brown Eyes (No. 21660E12; unpatented) and Pancho (No. 21610E04; unpatented). Reference is made to attached Chart A which compares certain characteristics of Revere with the same characteristics of Brown Eyes and Pancho. General comparisons are as follows:

1. In comparison to Brown Eyes, Revere has different inflorescence color, earlier natural season flower date, more upright branching pattern, taller plant height, and larger diameter across face of inflorescence. The inflorescence type, inflorescence form, and controlled flowering response of Revere are similar to those of Brown Eyes.

2. In comparison to Pancho, Revere has different inflorescence color, different inflorescence type, earlier natural season flower date, taller plant height, and larger diameter across face of inflorescence. The inflorescence form, branching pattern, and controlled flowering response of Revere are similar to those of Pancho.

In the following description, color references are made to The Munsell Limit Color Cascade, 1972 edition. The color values were determined between 10:30 and 11:00 A.M. on Oct. 14, 1975 under 120 foot-candle light intensity at Barberton, Ohio.

Botanical classification: *Chrysanthemum morifolium*, Ramat., cv Revere.

*Color (abaxial)*.—27-6 to 28-6.
*Color (adaxial)*.— 27-4 to 29-4, streaked and tipped with 41-10 to 41-15.

C. Reproductive organs
*Androecium*.—present disc florets; scant pollen.
*Gynoecium*.—present both ray and disc florets.

II. PLANT

A. General Appearance: semi-upright; medium height.
B. Duration and Texture: herbaceous; perennial.
C. Foliage
*Color (abaxial)*.—approximately 22-12 to 22-13.
*Color (adaxial)*.—approximately 22-11 overcast with white.
*Shape*.—spatulate; deeply lobed.
*Texture*.—glabrous.
*Venation*.—prominent.
*Margin*.—deeply serrated.

CHART A

COMPARISON OF REVERE, BROWN EYES, AND PANCHO

| CULTIVAR | INFLORESCENCE COLOR | INFLORESCENCE FORM AND TYPE | NATURAL SEASON FLOWER DATE | BRANCHING PATTERN | PLANT HEIGHT | CONTROLLED FLOWERING RESPONSE | DIAMETER ACROSS FACE OF INFLORESCENCE |
|---|---|---|---|---|---|---|---|
| Revere | Red bronze to yellow-bronze | Flat pompon | September 30 | Semi-upright | Medium, from 13 to 14 inches | 7 week | 2.25 to 2.75 inches |
| Brown Eyes | Copper bronze | Flat pompon | October 5 | Spreading | Short, from 9 to 10 inches | 7 week | 1.5 to 2.0 inches |
| Pancho | Orange bronze | Flat decorative | October 1 | Semi-upright | Short, from 10 to 12 inches | 7 week | 2.0 to 2.5 inches |

I. INFLORESCENCE

A. Capitulum
*Form*.—flat.
*Type*.—pompon.
*Permanence*.—14-21 days.
*Diameter across face*.—2.25 to 2.75 inches.
B. Corolla of ray floret
*Texture (adaxial)*.—glabrous.
*Appearance and form*.—ligulate.
*Arrangement*.—whorled on receptacle.
*Persistence*.—resists shatter.

We claim:

1. A new and distinct cultivar of chrysanthemum known by the cultivar name Revere and characterized particularly as to uniqueness by the combined characteristics of flat inflorescence form, reflexing slightly at maturity; pompon inflorescence type; two-toned red bronze and yellow bronze inflorescence color; diameter across face of inflorescence up to 2.75 inches; permanence of inflorescence ranging from 14 to 21 days; medium plant height; semi-upright branching pattern; average natural season flowering date of September 30 and average flowering response period of 7 weeks in photoperiodic controlled flowering programs.

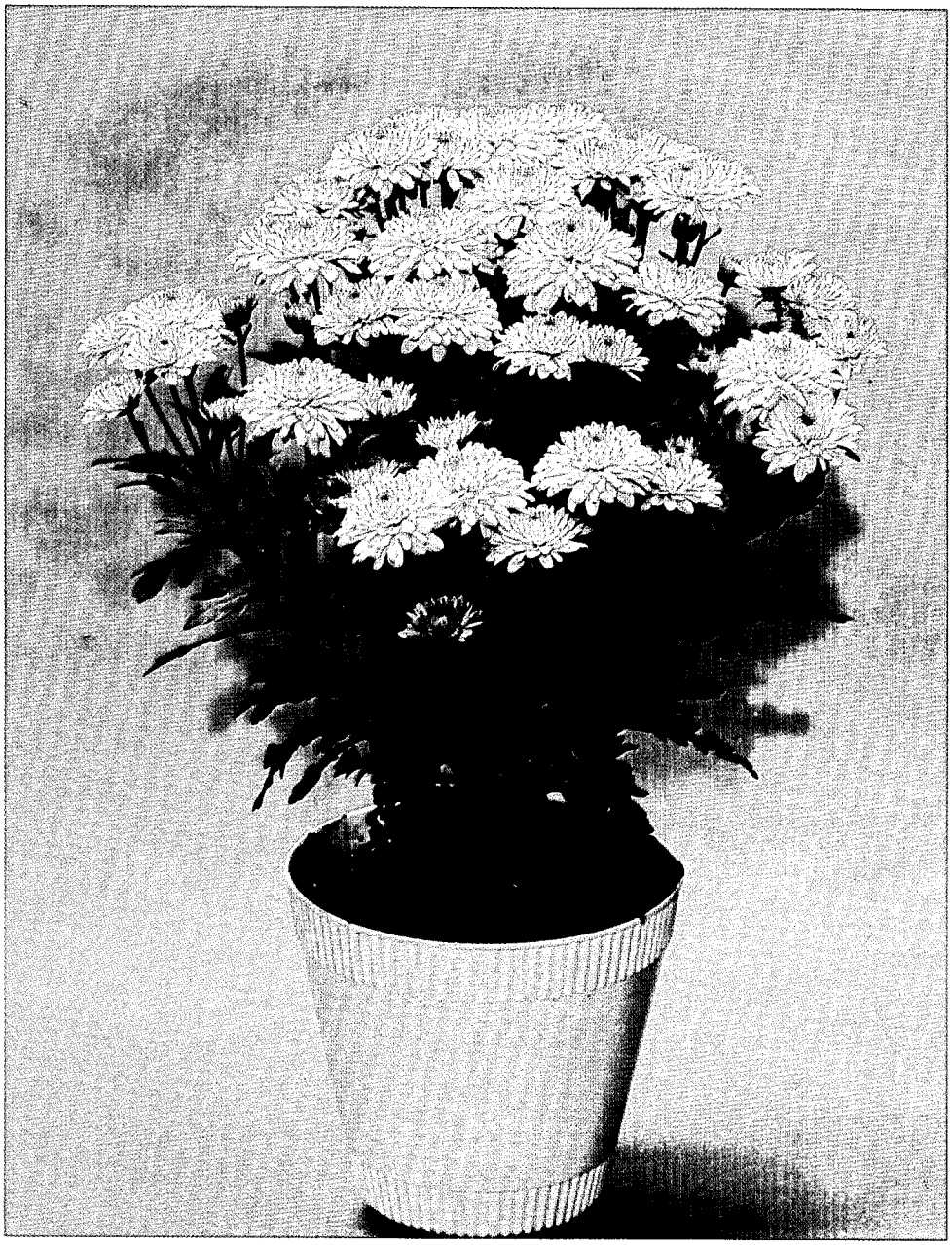

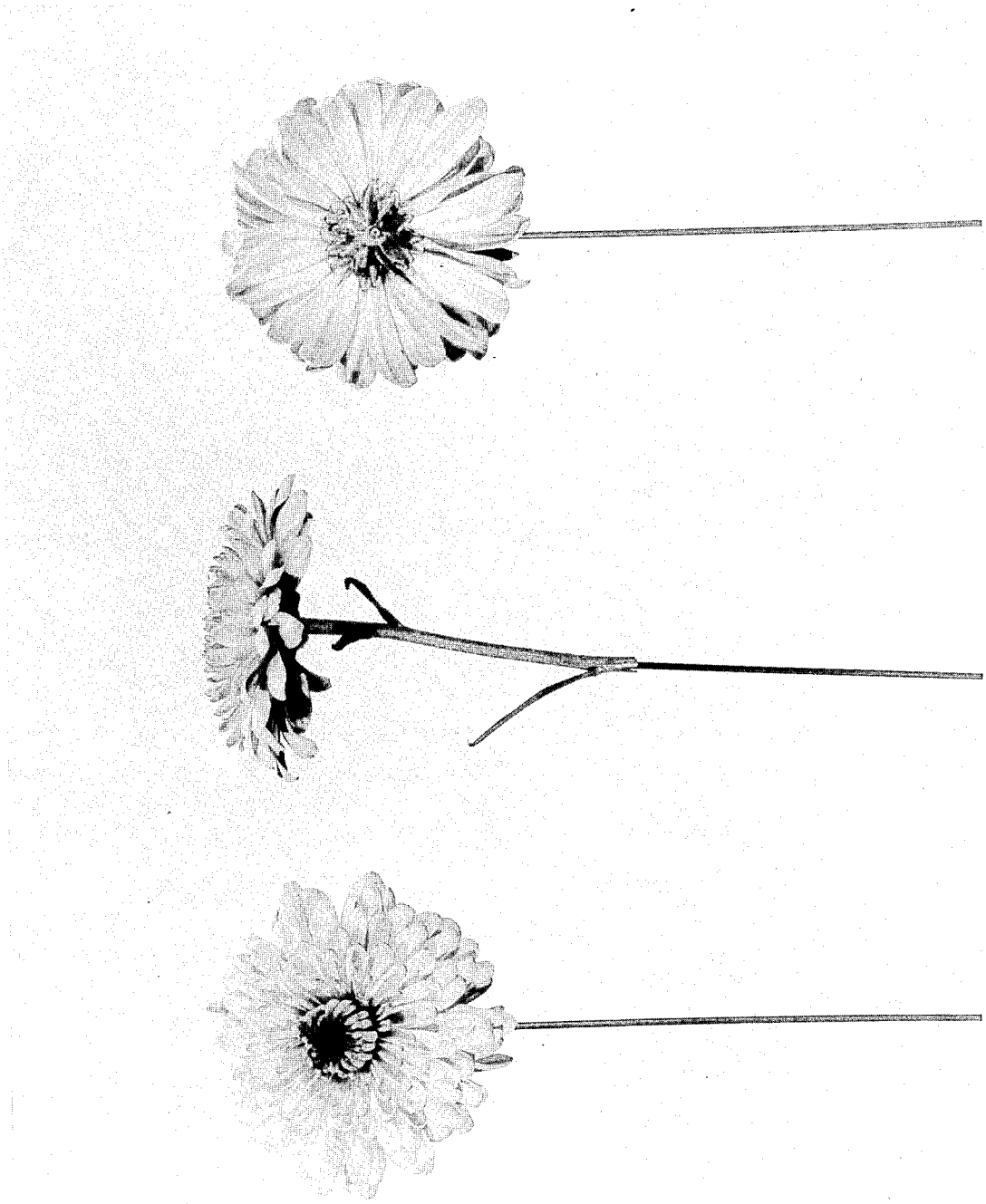

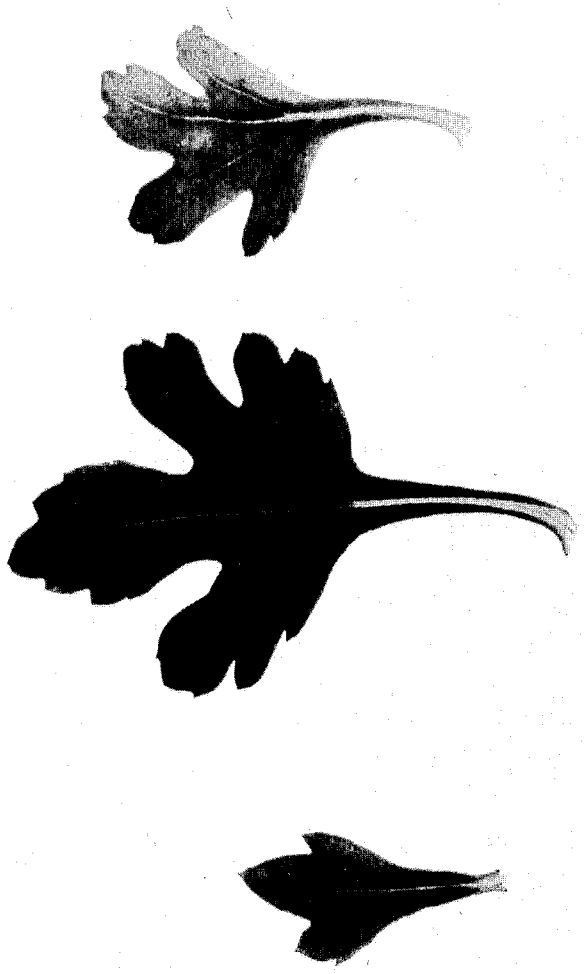

* * * * *